United States Patent [19]

Bhatia et al.

[11] 4,096,192

[45] * Jun. 20, 1978

[54] PROCESS FOR THE PREPARATION OF 2-METHYL-1,3-PROPANEDIOL

[75] Inventors: Kamlesh Kumar Bhatia, Newark; Charles Carmen Cumbo, Wilmington, both of Del.

[73] Assignee: E. I. Du Pont de Nemours and Company, Wilmington, Del.

[*] Notice: The portion of the term of this patent subsequent to Dec. 30, 1992, has been disclaimed.

[21] Appl. No.: 672,033

[22] Filed: Mar. 30, 1976

[51] Int. Cl.$^2$ .............................................. C07C 29/00
[52] U.S. Cl. .................................................... 568/866
[58] Field of Search .................................... 260/635 E

[56] References Cited

U.S. PATENT DOCUMENTS

| | | | |
|---|---|---|---|
| 3,929,915 | 12/1975 | Cumbo et al. | 260/635 E |
| 3,963,754 | 6/1976 | Cumbo et al. | 260/340.7 |
| 3,963,755 | 6/1976 | Cumbo et al. | 260/340.7 |
| 4,017,550 | 4/1977 | Kummer | 260/635 E |
| 4,024,197 | 5/1977 | Cumbo et al. | 260/635 E |

*Primary Examiner*—James O. Thomas, Jr.
*Assistant Examiner*—G. T. Breitenstein

[57] ABSTRACT

A process for the preparation of 2-methyl-1,3-propanediol (MPD) by recycling mixed diols from the process for the preparation of 1,4-butanediol from acrolein and aliphatic diols until the final product is essentially 1,4-butanediol and MPD.

11 Claims, No Drawings

PROCESS FOR THE PREPARATION OF 2-METHYL-1,3-PROPANEDIOL

BACKGROUND OF THE INVENTION

This invention relates to a unique process for preparing 2-methyl-1,3-propanediol (MPD). More specifically, this invention relates to a process for preparing essentially MPD from a mixture of MPD and another aliphatic diol.

In U.S. Pat. No. 3,929,915 a process is disclosed for reacting acrolein with 2-methyl-1,3-propanediol (MPD) followed by hydroformylation, hydrolysis and hydrogenation to give 1,4-butanediol and MPD. While the MPD produced is recycled back to the initial reaction, the MPD initially required is not readily available and there is no convenient process for its preparation. There is, therefore, a need for a convenient process that can be advantageously used to prepare MPD for use in the above reactions for converting acrolein to 1,4-butanediol.

SUMMARY OF THE INVENTION

It has now been found that 2-methyl-1,3-propanediol (MPD) can be prepared by a process which comprises (1) reacting acrolein with an aliphatic diol with 3 to 7 carbon atoms under conventional conditions to prepare a cyclic acetal, (2) hydroformylating the cyclic acetal under conventional conditions in the presence of a rhodium complex catalyst to prepare the linear and branched aldehydes of the cyclic acetal, (3) hydrogenating and hydrolyzing under conventional conditions said aldehydes of the cyclic acetal to prepare 1,4-butanediol, MPD and another diol, (4) separating MPD and the other diol from 1,4-butanediol, (5) recycling MPD and the other diol back to step (1) to react with acrolein in place of the aliphatic diol until the final product after hydrogenation and hydrolysis consists essentially of 1,4-butanediol and 2-methyl-1,3-propanediol (MPD) and (6) separating the 2-methyl-1,3-propanediol.

The first step of the process of the present invention is described and illustrated below using 1,3-butanediol as a starting material and reacting it with acrolein. It will be understood that similar reaction will occur with other diols within the scope of the present invention.

STEP 1 - ACROLEIN REACTION

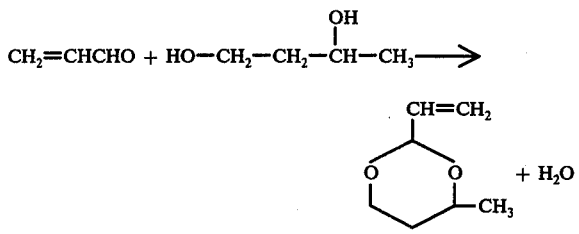

The acrolein can also be reacted with other diols using any conventional conditions such as those discussed in U.S. Pat. Nos. 2,729,650 issued Jan. 3, 1956 to Habeshaw et al.; 2,840,615 issued June 24, 1958 to Stautzenberger; 2,987,524 issued June 6, 1961 to Fischer et al.; 2,566,559 issued Sept. 4, 1951 to Dolnick & Potash and the like. As described in U.S. Pat. No. 2,566,559, acrolein is reacted with MPD at a molar ratio of MPD to acrolein of 4 to 5:1.

In one preferred process, the acrolein is reacted with 1,3-butanediol in a suitable solvent such as benzene and in the presence of a weak acid catalyst such as a small amount of polyphosphoric acid with the azeotropic distillation of water.

The acrolein may be obtained commercially or it may be prepared from propylene, for example, as described in U.S. Pat. Nos. 3,065,264 and 3,087,964 issued Nov. 20, 1962 and Apr. 30, 1963, respectively, to Koch et al.; 3,387,038 issued June 4, 1968 to Koch; 3,799,978 issued Mar. 26, 1974 to O'Hara et al. and so on. In such processes, propylene is oxidized in the presence of water and oxygen to yield acrolein using molybdenum containing catalysts, generally bismuth molybdate catalysts.

The 1,3-butanediol which is available commercially may be prepared as is known in the art by the condensation of acetaldehyde followed by hydrogenation of the aldol condensation product.

The diols of the process of the present invention are any aliphatic 1,3-diols having a boiling point sufficiently lower than 1,4-butanediol to make a separation possible of the diol from 1,4-butanediol. The diols most readily available are aliphatic diols with 3 to 7 carbon atoms. Representative examples of the diols of the present invention include 1,3-butanediol, 1,3-propanediol, 2,2-dimethyl propanediol and 2-methyl-2,4-pentanediol. The preferred diols of the present invention are 1,3-butanediol, 1,3-propanediol, 2,2-dimethyl propanediol and 2-methyl-2,4-pentanediol.

STEP 2 - Hydroformylation

In the second step of this process, the cyclic vinyl acetal from Step 1 is reacted under conventional conditions with hydrogen and carbon monoxide in the presence of a rhodium complex to prepare the corresponding aldehydes. This is illustrated in the equations that follow with 2-vinyl-4-methyl-1,3-dioxane:

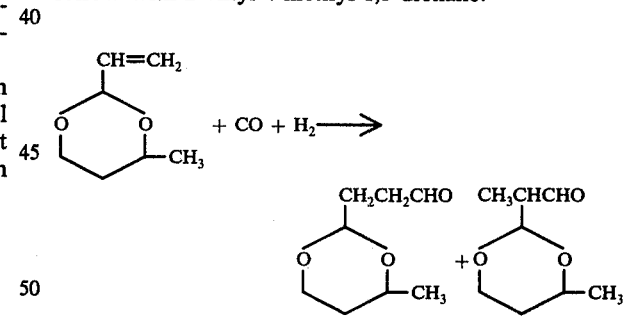

Aside from the aforesaid catalyst, any conventional hydroformylation reaction conditions can be used to carry out this reaction such as those described in U.S. Pat. Nos. 3,527,809 issued Sept. 8, 1970 to Pruett et al.; 3,880,241 issued Mar. 31, 1959 to V. L. Hughes; 2,729,650 issued Jan. 3, 1956 to Haveshaw et al.; 3,239,566 issued Mar. 8, 1966 to L. H. Slaugh and R. D. Mullineaux; British Pat. No. 801,734 issued Sept. 17, 1958 to Esso Research and Engineering and the like.

In a preferred embodiment, the cyclic acetal is reacted with hydrogen and carbon monoxide at a molar ratio of $H_2:CO$ of 0.9:1 to 1.2:1, preferably 1:1. At ratios lower than 0.9:1, the reaction rates are too slow for commercial utility; at ratios higher than 1.2:1, hydrogenation of the cyclic acetal occurs as an undesired side reaction. The highest yields of 1,4-butanediol and 2- methyl-1,3-propanediol together are obtained at the preferred ratio.

The hydroformylation reaction is carried out in the presence of a rhodium concentration of $1 \times 10^{-3}$ to $6 \times 10^{x3}$ g atoms per mole of VMD, preferably $1 \times 10^{-3}:1$ to $2 \times 10^{-3}:1$. At the preferred ratios, optpimum yields and reaction rates result. The linear to branched isomer ratio that results influences the number of cycles required to produce essentially only MPD. The lower the linear to branched isomer, the lower the number of cycles required to attain essentially all MPD. In order to attain lower linear to branched isomer ratios that result in optimum preparation of MPD, high carbon monoxide levels and low ligand levels are employed. The rhodium complex catalyst forms in situ when rhodium in the form of $Rh_6(CO)_{16}$ is added to the hydroformylation reaction mixture containing the ligand described below. The same rhodium carbonyl complex with a trialkyl phosphite may also be prepared first and then added to the reaction mixture.

The phosphite ligand used in the hydroformylation reaction has the formula $$\begin{array}{c} OR_1 \\ | \\ P-OR_2 \\ | \\ OR_3 \end{array}$$

wherein $R_1$, $R_2$ and $R_3$ are the same or different phenyl, substituted phenyl or alkyl groups having 1 to 12 carbon atoms such as, for example, p-chlorophenyl, p-tolylphenyl, methyl, ethyl, propyl, octyl, pentyl, decyl, dodecyl and the like. In the process of this invention, $R_1$, $R_2$ and $R_3$ are preferably phenyl. For ease of operation, it is preferred that $R_1$, $R_2$ and $R_3$ are the same. When $R_1$, $R_2$ and $R_3$ are alkyl it is preferred that they be the same alkyl groups having 1 to 3 carbon atoms such as trimethyl phosphite, triethyl phosphite, tri-n-propyl phosphite and triisopropyl phosphite since these materials are low boiling and easily separated, purified and recycled into the system. However, high boiling phosphites within the scope of the above formula may also be used including tri-n-butyl phosphite, triisooctyl phosphite, dimethyldodecyl phosphite, tridecyl phosphite, triphenyl phosphite, methylethylpropyl phosphite, dimethyl phenyl phosphite, methylpropyl phenyl phosphite a well as any other combination within the definition of the above formula and mixtures of any of them.

The phosphite ligand forms a complex with rhodium and carbon monoxide as described in U.S. Pat. No. 3,527,809, and this complex catalyzes the hydroformylation reaction. An excess of the phosphite over that which is required to complex with the rhodium must be used in order to prevent isomerization of the double bond in the cyclic acetal aldehyde (vinyl methyl dioxane) and to maximize the yield of linear aldehyde produced in the reaction. The excess ligand is also necessary to insure the stability of the rhodium catalyst throughout the reaction. Generally, a molar ratio of phosphite ligand to rhodium of from 5:1 to 50:1 is employed. In order to obtain optimum reaction rates and produce a product which will favor the formation of butanediol upon hydrolysis and hydrogenation, it is preferred that a ligand:rhodium molar ratio of from 10:1 to 30:1 be employed.

The hydroformylation reaction may be carried out in any suitable reactor including a simple low pressure reactor. For ease of operation, it is preferred that the reaction be carried out in a continuous stage reactor through which the acetal flows cocurrently to the flow direction of the carbon monoxide and hydrogen gas. The reactor pressure should be from about 20 to 150 psig, preferably 30 to 110 psig. The reactor temperature should be from about 85° to 115° C, preferably 100° to 110° C and the residence time in the reactor should be from 0.5 to 5 hours, preferably 1 to 2 hours. At the preferred conditions, the highest yields and best reaction rates are obtained.

When low boiling trialkyl phosphites are used, the ligand is stripped off in any suitable manner, after the product stream exists from the reaction. The reaction product is preferably fed into a ligand stripper column maintained at a pressure of 10 mm and a temperature of 110° C. Excess ligand is removed and recycled to the reaction. The product stream is then fed to an aldehyde vaporizer column maintained at a pressure of about 8 mm and a temperature of 120° C. Aldehyde product is distilled off to be used in the hydrolysis-hydrogenation reaction. In order to prevent aldehyde decomposition, the temperature in this step should not exceed 120° C and the aldehyde residence time should be less than five minutes. The bottom stream from this separation step contains some high boiling byproducts which are unavoidably formed as well as all of the rhodium catalyst. This stream is recycled to the reactor after removing a small portion, about one-eighth, of the stream as a purge stream to control the buildup of high boilers. While it has been disclosed that the presence of these high boiling constituents is advantageous in some cases such as, for example, disclosed in U.S. Pat. No. 3,527,809 issued to Pruett on Sept. 8, 1970, it has been found that an acceptable maximum concentration of high boilers in this invention is about 50%, preferably 25%.

Where the ligand is triphenyl phosphite or tritolyphenyl phosphite or trichlorophenyl phosphite, the ligand is high boiling relative to the product and is not to be stripped off the same way as the trialkyl phosphite. For example, the preferred triphenyl phosphite is separated from the reaction product by distilling off the aldehydes produced leaving the high boiling ligand with the catalyst and high boiling byproducts.

STEP 3 - HYDROLYSIS/HYDROGENATION

In the third step of this process, the hydroformylation reaction product is hydrolyzed and hydrogenated to prepare 1,4-butanediol and 2-methyl-1,3-propanediol.

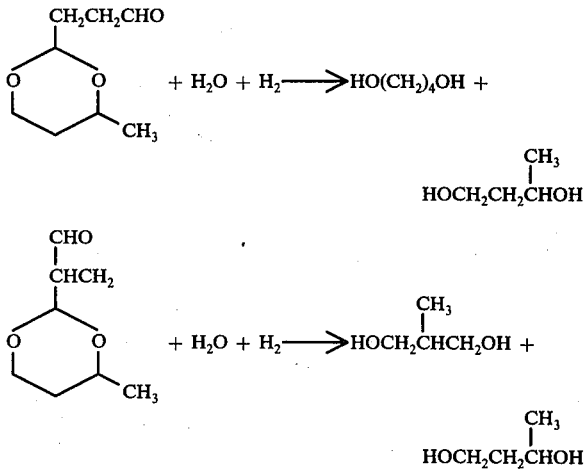

The acetal-aldehyde hydroformylation reaction product can be hydrolyzed and hydrogenated using any of the conventional procedures including those described in U.S. Pat. Nos. 2,729,650; 2,888,492 issued May 26, 1959 to Fischer et al.; 2,721,223 issued Oct. 18, 1955 to Arundale & Mikeska and the like. In a preferred embodiment, water is mixed with the acetal-aldehyde hydroformylation reaction product and the mixture is fed into a hydrogenation reactor at a temperature of 30° to 130° C, a pressure of 100 to 5,000 psig and at a water: aldehyde molar ratio of 1:1 to 20:1. The aldehyde functional group is reduced to the corresponding alcohol in the presence of a catalytic amount of any hydrogenation catalyst such as Raney nickel, for example. As the reaction is continued, the acetal ring splits to yield 1,4-butanediol (BAD), 2-methyl-1,3-propanediol (MPD) and another diol from which the BAD can be separated as Step 4 of the process of the present invention by conventional distillation techniques. The mixed diols prepared according to the process of the present invention can be readily separated from BAD by conventional distillation methods. Boiling points for some diols of this invention are listed below:

| Diol | B.Pt. at 760 mm of Hg |
|---|---|
| 1,4-butanediol | 230° C |
| 2-methyl-1,3-propanediol | 214° C |
| 1,3-butanediol | 207° C |
| 2,2-dimethyl propanediol | 206° C at 747 mm Hg |
| 2-methyl-2,4-pentanediol | 197° C |
| 1,3-propanediol | 213° C |

STEP 5

The MPD and the other diol, for example, 1,3-butanediol, formed by hydroformylation can then be recycled and used in the preparation of the cyclic acetal of Step 1. The cyclic acetal formed as a result of the use of said MPD and 1,3-butanediol is 2-vinyl-5-methyl-1,3-dioxane (from the MPD) and 2-vinyl-4-methyl-1,3-dioxane (from 1,3-butanediol).

The diols that result from Step 3 in addition to BAD and MPD and the diol that was initially reacted. The mixture of diols produced are difficult to separate in Step 4 because of the small difference in boiling points between MPD and the diol initially reacted.

However, in the present invention, this need for separation is avoided because after a period of time involving a number of cycles of operation when steady state conditions are reached and the diols produced are essentially only 1,4-butanediol and MPD which can be readily separated from each other the MPD portion of the product is a mixture of diols consisting essentially of MPD. For example, a product consisting of 1,4-butanediol and a mixture of diols (essentially all MPD) wherein the mixture is from 75 to 98% by weight MPD is attained after 15 cycles while from 90 to 99% by weight or more MPD in the mixture of diols is attained after 25 cycles.

Thus, depending on the isomer ratio used after 15 cycles, it is possible to attain a mixture of diols in the product containing 99% by weight of more MPD. Generally, however, the mixture of diols by the process of this invention comprise 75 to 99% by weight or more MPD after 15 to 25 cycles. As low as 8 cycles produces a mixed diol with greater than 90% by weight MPD.

The higher the linear to branched chain isomer ratio, the greater the number of cycles required to achieve a maximum of MPD preparation. The lower the linear to branched chain isomer ratio the lower the number of cycles required to achieve a maximum MPD preparation.

STEP 6

2-methyl-1,3-propanediol (MPD) is separated from the reaction product by conventional distillation techniques. The recovered MPD is useful in the preparation of 1,4-butanediol which is useful as a crosslinking agent in the preparation of polyurethane polymers and also readily converted to tetrahydrofuran which is useful as a solvent. MPD is also useful in the preparation of polymers.

In the process of the invention the recycling of the mixed diols, which include MPD and the starting diol, results in the preparation of essentially only MPD with the 1,4-butanediol. What is meant by essentially MPD is at least 90% MPD in the product after removal of the 1,4-butanediol. After sufficient recycling the MPD does reach essentially 100%.

The process described above may be operated as a sequential batch operation or a continuous operation. For economic reasons, continuous operation is preferred.

ACROLEIN PREPARATION

A vapor mixture of propylene, oxygen and water in a mole ratio of 2:1:3 (propylene:oxygen:water) is fed continuously into the reactor at a feed rate of 4 liters of vapor per 100 grams of catalyst per minute (corrected to standard temperature and pressure). The reactor contains a bismuth-promoted strontium-molybdenum precipitated catalyst composed of oxides and molybdenum, strontium and bismuth in a mole ratio of 1.05:1:0.05 (molybdenum:strontium:bismuth). The reaction zone temperature is maintained at 500° C. As determined by gas chromatography, 29% of the propylene is converted to yield 53% acrolein based on the amount of propylene converted. The exit gas stream also contains $CO$, $CO_2$, $O_2$, unreacted propylene and a very small amount of other oxygenated compounds.

The following examples are submitted to further illustrate the process of this invention. All percentages are by weight unless otherwise indicated.

EXAMPLE 1

Step 1 - Preparation of 2-Vinyl-4-Methyl-1,3-Dioxane (4-VMD)

A 227 g reaction mixture which contains 1.47 moles of 1,3-butanediol (1,3-BAD) and 1.62 moles of acrolein is reacted at a temperature of 55° C, by passing it through a column of 10 ml Dowex 50WX12 (sulfonated crosslinked polystyrene acidic cationic exchange resin manufactured by the Dow Chemical Co.) at a rate of 1.5 g/min. The reaction product separates into 2 layers - an upper layer containing 1.25 moles 2-vinyl-4-methyl-1,3-dioxane (4-VMD), 0.26 mole acrolein and 0.27 mole of 1,3-BAD. The lower layer contains 0.03 mole 4-VMD, 0.02 mole acrolein and 0.10 mole 1,3-BAD dissolved in 1.27 moles water. The conversion of 1,3-BAD to the acetal product is 87.0%. Of the 1,3-BAD in the reaction mixture, 11.6% is recovered in addition to the 87% converted to acetal. The remaining 1.4% of 1,3-BAD is converted to high-boiling products and lost in handling.

The reaction product, 4-VMD, and unreacted starting materials are separated by distillation, giving 0.275 mole of acrolein, 0.165 mole of 1,3-BAD and 1.25 mole of 4-VMD. The recovered acrolein and 1,3-BAD are then recycled to acetal preparation.

Step 2 - Hydroformylation of 2-Vinyl-4-Methyl-1,3-Dioxane

The reaction product, 160 g (1.25 moles) of 2-vinyl-4-methyl-1,3-dioxane, 4-VMD, from Step 1 is charged into a 300 cc stainless steel magne drive autoclave in an atmosphere of dry nitrogen, with 0.12 g $RH_6(CO)_{16}$ and 6.0 g triphenyl phosphite. The autoclave is then charged with a 1:1 molar ratio of carbon monoxide-hydrogen gas to a pressure of 80 psig. The contents are heated to 110° C and maintained throughout the reaction. After 60 minutes the autoclave is cooled and the excess gases are vented. The liquid contents are removed and analyzed by gas-liquid phase chromatography. Analysis of the product shows a 100% conversion of 2-vinyl-4-methyl-1,3-dioxane and a linear to branched chain isomer ratio of 0.89. The product analysis in grams and in mole percent is given below:

| | | |
|---|---|---|
| 2(3'-propanal)-4-methyl-1,3-dioxane | 85.5% | 169.0 g |
| 2(2'-propanal)-4-methyl-1,3-dioxane | 11.2% | 22.2 g |
| 2-ethyl-4-methyl-1,3-dioxane | 3.2% | 5.2 g |

Distillation of the above reaction mixture at 10 mm Hg gives 163 g 2(3'-propanal)-4-methyl-1,3-dioxane, 21.5 g 2(2'-propanal)-4-methyl-1,3-dioxane and 5.2 g 2-ethyl-4-methyl-1,3-dioxane. The pot residue containing the remainder of the linear aldehyde and high boiler is recycled back to the hydroformylation reactor.

Step 3 - Hydrogenation/Hydrolysis of Aldehyde Acetals to Diols

The 189.7 g distillate from the previous step containing 163 g of 2-(3'-propanal)-4-methyl-1,3-dioxane, 21.5 g of 2-(2'-propanal)-4-methyl-1,3-dioxane and 5.2 g of 2-ethyl-4-methyl-1,3-dioxane is mixed with 95 g of water and charged to a stirred autoclave with 25 g of Raney nickel and 25 g of Dowex 50 (sulfonated crosslinked polystyrene acidic cationic exchange resin manufactured by the Dow Chemical Co.). This is heated to 85° C under 1500 psig $H_2$ for 60 minutes. The resulting product is distilled, giving 88.7 g 1,4-butanediol, and a lower-boiling cut containing 10.7 g 2-methyl-1,3-propanediol and 106 g 1,3-butanediol. The ratio of linear to branched chain isomer was 0.89. The latter cut is recycled to the acetal formation step.

Step 4 - Preparation of MPD Using Recycled Diol Mixtures

Acetal, formed as described in Step 1, is hydroformylated as described in Step 2. The mixture of MPD and 1,3-BAD from the hydrogenation/hydrolysis of Step 3 is augmented with sufficient recovered diol from Step 1 to produce 1,47 moles of diol as a mixture of MPD and 1,3-BAD. This diol mixture is recycled to acetal formation. The amount of MPD in this diol mixture increases with each recycle. After 15 cycles the MPD content of the diol mixture serving as feed to the acetal formation step is greater than 75% and after 25 cycles it is greater than 90% MPD.

Repeating the above example except at higher hydroformylation pressure decreases the linear to branched ratio, thereby increasing the MPD produced by hydroformylation

EXAMPLE 2

Step 1 - Preparation of 2-Vinyl-4-Methyl-1,3-Dioxane (4-VMD)

A 227 g reaction mixture which contained 1.47 moles of 1,3-butanediol (1,3-BAD) and 1.62 moles of acrolein is reacted at a temperature of 55° C, by passing it through a column of 10 ml Dowex 50WX12 resin (sulfonated crosslinked polystyrene acidic cationic exchange resin manufactured by the Dow Chemical Co.) at a rate of 1.5 g/min. The designation 50WX12 indicates pore size and degree of crosslinking. The reaction product separates into 2 layers - an upper layer containing 1.25 moles 2-vinyl-4-methyl-1,3-dioxane (4-VMD), 0.26 mole acrolein and 0.07 mole 1,3-BAD. The lower layer contains 0.03 mole 4-VMD, 0.02 mole acrolein and 0.10 mole 1,3-BAD dissolved in 1.27 moles water. The conversion of 1,3-BAD to the acetal product is 87.0%. Of the 1,3-BAD in the reaction mixture, 11.6% is recovered in addition to the 87% converted to acetal. The remaining 1.4% of 1,3-BAD is converted to high-boiling products and lost in handling.

The reaction product, 4-VMD, and unreacted starting materials are separated by distillation, giving 0.275 mole of acrolein, 0.165 mole of 1,3-BAD and 1.25 mole of 4-VMD. The recovered acrolein and 1,3-BAD are then recycled to acetal preparation.

Step 2 - Hydroformylation of 2-Vinyl-4-Methyl-1,3-Dioxane

The reaction product, 16 g (1.25 mole) of 2-vinyl-4-methyl-1,3-dioxane, is charged into a 400 cc glass autoclave equipped with a magnetic stirrer and charged, in an atmosphere of dry nitrogen, with 0.27 g $Rh_6(CO)_{16}$, and 2.7 cc of trimethyl phosphite. The autoclave is then charged with a 1:1 molar ratio of carbon monoxide-hydrogen gas to a pressure of 105 psig. The contents are heated to 95° C and maintained throughout the reaction. After 3.0 hours, the autoclave is cooled an the excess gases are vented. The liquid contents are removed and analyzed by gas-liquid phase chromatography. Analysis of the mixture gave a linear to branched chain isomer ratio of 0.67 and the following mole percent and weights of products:

| | | |
|---|---|---|
| 2(3'-propanal)-4-methyl-1,3-dioxane | 66.5% | 131.4 g |
| 2(2'-propanal)-4-methyl-1,3-dioxane | 32.5% | 64.3 g |
| 2-ethyl-4-methyl-1,3-dioxane | 1.0% | 1.7 g |

Distillation of the mixture to remove aldehydes from catalyst, ligand and byproducts at 10 mm Hg gave 63.5 g 2(2'-propanal)-4-methyl-1,3-dioxane and 126.9 g 2(3'-propanal)-4-methyl-1,3-dioxane and 1.7 g of 2-ethyl-4-methyl-1,3-dioxane.

Step 3 - Hydrogenation/Hydrolysis of Aldehyde Acetals to Diols

The 192.1 g distillate from the previous step containing 126.9 g 2-(3'-propanal)-4-methyl-1,3-dioxane, 63.5 g 2-(2'-propanal)-4-methyl-1,3-dioxane and 1.7 g 2-ethyl-4-methyl-1,3-dioxane is mixed with 96 g of water and charged to a stirred autoclave with 25 g of Raney nickel and 25 g of Dowex 50 (sulfonated crosslinked polystyrene acidic cationic ion exchange resin manufactured by the Dow Chemical Co). This is heated to 85° C under 1500 psig $H_2$ for 60 minutes. The resulting product is distilled, giving 69 g 1,4-butanediol, and another cut containing 33 g 2-methyl-1,3-propanal and 107 g 1,3-butanediol. The latter cut is recycled to the acetal formation step.

Step 4 - Preparation of MPD Using Recycled Diol Mixtures

Acetal, formed as described in Step 1, is hydroformylated as described in Step 2. Following hydrogenation/hydrolysis of the hydroformylation product as described in Step 3, a 132 g portion (1.47 moles) of the resulting diol mixture is recycled to acetal formation. Upon each repetition of this cycle, the amount of MPD in the diol recycle feed to acetal formation increases. After 15 cycles, the MPD content of the diol feed mixture is more than 98% and after 25 cycles the MPD content of the diol feed mixture is greater than 99.8%.

Repeating the above example at higher hydroformylation pressure would increase the MPD produced in hydroformylation and reduce the cycles needed to attain a given percent MPD.

While the invention has been described in considerable detail in the foregoing, it is to be understood that such detail is solely for the purpose of illustration and that variations can be made by those skilled in the art without departing from the spirit and scope of the invention except as set forth in the claims.

What is claimed is:

1. A continuous process for the preparation of 2-methyl-1,3-propanediol which comprises
   (a) reacting acrolein with a 1,3-aliphatic diol with 3 to 7 carbon atoms other than 2-methyl-1,3-propanediol under conventional conditions to prepare a cyclic acetal;
   (b) hydroformylating the cyclic acetal in the presence of a rhodium complex catalyst comprising rhodium carbonyl and a phosphite ligand of the formula

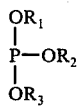

wherein $R_1$, $R_2$ and $R_3$ are the same or different phenyl, substituted phenyl or alkyl groups having 1 to 12 carbon atoms under conventional conditions to prepare the aldehyde of the cyclic acetal;
   (c) hydrogenating and hydrolyzing the aldehyde of the cyclic acetal in the presence of a hydrogenation catalyst and an ion exchange catalyst to prepare 1,4-butanediol and a mixture of diols;
   (d) separating the mixture of diols from 1,4-butanediol;
   (e) recycling said mixture back to step (a) to react with acrolein in place of the diol of (a) for a number of cycles until a product consisting of 1,4-butanediol and essentially 2-methyl-1,3-propanediol; and
   (f) separating and recovering the 2-methyl-1,3-propanediol.

2. The process of claim 1 wherein the aliphatic diol is 1,3-butanediol.

3. The process of claim 1 wherein the aliphatic diol is 2,2'-dimethyl propanediol.

4. The process of claim 1 wherein the aliphatic diol is 2-methyl-2,4-pentanediol.

5. The process of claim 1 wherein the aliphatic diol is 1,3-propanediol.

6. The process of claim 1 wherein the composition of the 2-methyl-1,3-propanediol in the final product is from 90 to 99% by weight of more 2-methyl-1,3-propanediol and the remainder is the starting aliphatic diol.

7. The process of claim 6 wherein the aliphatic diol is 1,3-butanediol.

8. The process of claim 1 wherein the composition of the 2-methyl-1,3-propanediol in the final product is 99% or more 2-methyl-1,3-propanediol and the remainder is the starting aliphatic diol.

9. The process of claim 8 wherein the aliphatic diol is 1,3-butanediol.

10. The process of claim 1 wherein the rhodium concentration is $1.0 \times 10^{-3}$ to $6.0 \times 10^{-3}$ gram atoms per mole of the cyclic acetal.

11. The process of claim 1 wherein the aliphatic diol is 1,3-butanediol, 1,3-propanediol, 2,2-dimethyl propanediol or 2-methyl-2,4-pentanediol.

* * * * *

UNITED STATES PATENT OFFICE
CERTIFICATE OF CORRECTION

PATENT NO. : 4,096,192
DATED : June 20, 1978
INVENTOR(S) : Kamlesh Kumar Bhatia and Charles Carmen Cumbo It is certified that error appears in the above-identified patent and that said Letters Patent are hereby corrected as shown below:

Column 2, line 37, after "complex" add -- catalyst --.
Column 3, line 5, "$10^{X3}g$" should be -- $10^{-3}g$ --.
Column 3, line 6, "otpimum" should be -- optimum --.
Column 4, line 13, "exists" should be -- exits --.
Column 5, line 42, "and MPD" should be -- are MPD --.
Column 5, line 61, "of" should be -- or --.
Column 10, line 27, Claim 6, "of" should be -- or --.

Signed and Sealed this

Twenty-seventh Day of February 1979

[SEAL]

Attest:

RUTH C. MASON
Attesting Officer

DONALD W. BANNER
Commissioner of Patents and Trademarks